(12) United States Patent
Ridder

(10) Patent No.: US 7,288,767 B2
(45) Date of Patent: Oct. 30, 2007

(54) METHOD AND A SPECTROMETER FOR QUANTITATIVE DETERMINATION OF A CONSTITUENT IN A SAMPLE

(75) Inventor: Carsten Ridder, Hornslet (DK)

(73) Assignee: Foss Analytical A/S, Hillerod (DK)

(*) Notice: Subject to any disclaimer, the term of this patent is extended or adjusted under 35 U.S.C. 154(b) by 301 days.

(21) Appl. No.: 10/514,628

(22) PCT Filed: May 28, 2003

(86) PCT No.: PCT/DK03/00355

§ 371 (c)(1),
(2), (4) Date: Jun. 29, 2005

(87) PCT Pub. No.: WO03/100394

PCT Pub. Date: Dec. 4, 2003

(65) Prior Publication Data

US 2005/0279924 A1    Dec. 22, 2005

(30) Foreign Application Priority Data

May 28, 2002  (DK) .............................. 2002 00817

(51) Int. Cl.
*G01J 5/02* (2006.01)

(52) U.S. Cl. .............................. 250/339.07; 250/341.8

(58) Field of Classification Search ............. 250/336.1, 250/338.1, 338.5, 339.01, 339.06, 339.07, 250/339.11, 339.13, 341.8; 356/320, 328
See application file for complete search history.

(56) References Cited

U.S. PATENT DOCUMENTS

| 4,236,075 A | 11/1980 | Nexo et al. |
| 4,744,657 A * | 5/1988 | Aralis et al. ................ 356/319 |
| 5,243,546 A | 9/1993 | Maggard |
| 5,708,593 A | 1/1998 | Saby et al. |

OTHER PUBLICATIONS

International Search Report.

* cited by examiner

Primary Examiner—David Porta
Assistant Examiner—Mark R Gaworecki
(74) Attorney, Agent, or Firm—Foley & Lardner LLP

(57) ABSTRACT

The present invention relates to a method of determining a constituent of a sample and more specifically, to a method of correcting an absorbance value for a spectrometer. The method is especially applicable in connection with spectrometric analysis instruments for quantitatively determining the chemical composition of fluids, e.g. the content of fat, protein lactose or urea, in food products, especially in raw milk or dairy products. The method is based upon a measurement of one or more selected ranges of a spectrum, providing an absorption spectrum of the product. The method may be applicable in connection with all spectroscopic instruments giving rise to specific ranges of a spectrum, such as UV, VIS, NIR, IR, NMR, MS, etc.). Typically, the spectrum will be a MID-IR absorption spectrum.

34 Claims, 2 Drawing Sheets

Figure 1:
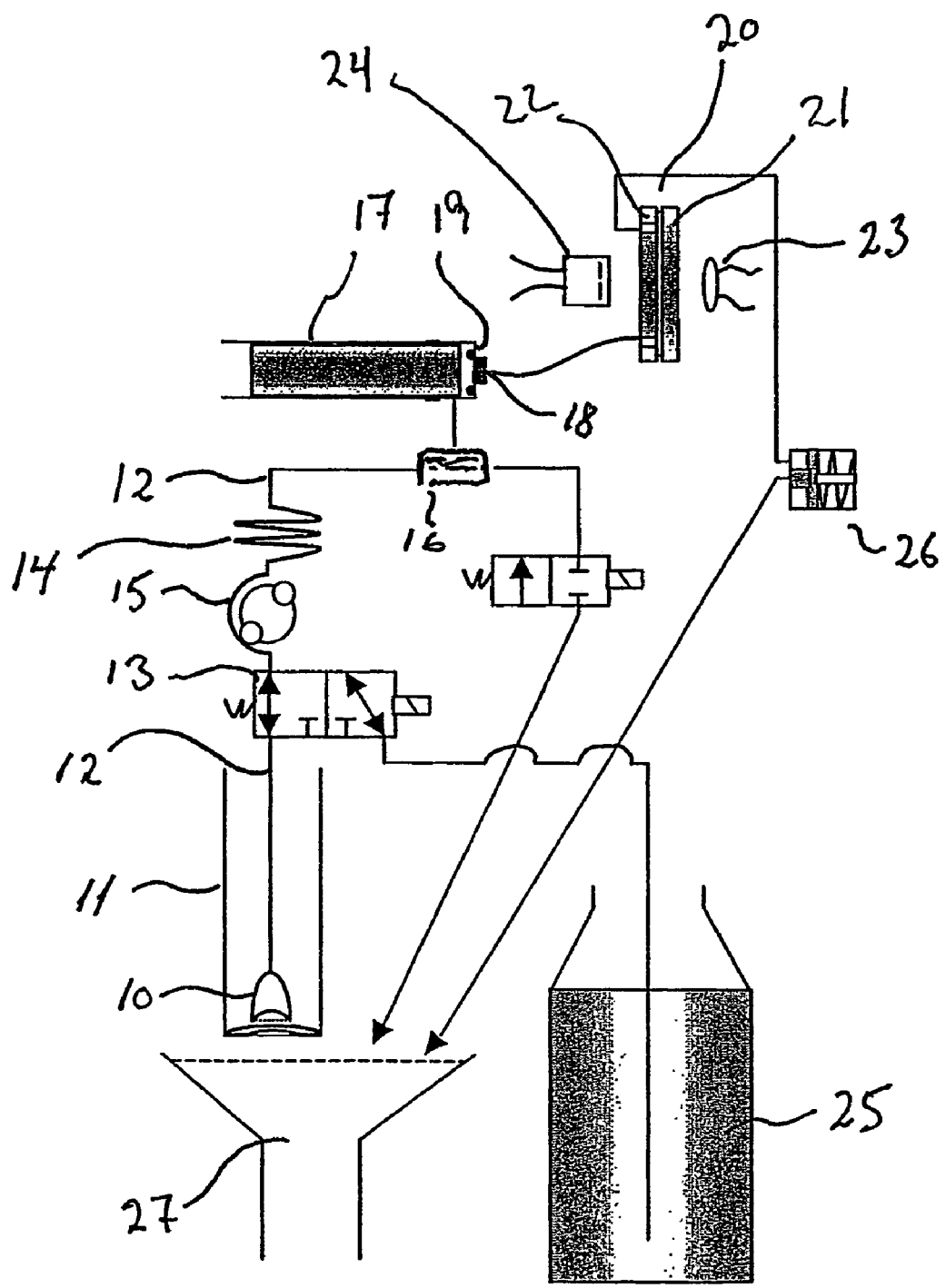

METHOD AND A SPECTROMETER FOR QUANTITATIVE DETERMINATION OF A CONSTITUENT IN A SAMPLE

TECHNICAL FIELD

The present invention relates to a method of determining a constituent of a sample and more specifically, to a method of correcting an absorbance value for a spectrometer. The method is especially applicable in connection with spectrometric analysis instruments for quantitatively determining the chemical composition of fluids, e.g. the content of fat, protein, lactose or urea, in food products, especially in raw milk or dairy products. The method is based upon a measurement of one or more selected ranges of a spectrum, providing an absorption spectrum of the product. The method may be applicable in connection with all spectroscopic instruments giving rise to specific ranges of a spectrum, such as UV, VIS, NIR, IR, NMR, MS, etc.). Typically, the spectrum will be a MID-IR absorption spectrum.

BACKGROUND OF THE INVENTION

The method is specifically intended for filter-based spectrometers, which typically comprises an infrared light source, and an infrared detector, and there between a number of optical filters, which may be inserted into the optical light path. A sample measurement cell comprising two glass plates defining a storage space therein between for storage of a sample to be analysed, is arranged between the light source and the detector. During use, the cell is filled with the sample e.g. milk, and the light transmitted from the light source through the sample is detected.

Typically, the concentration of the constituent e.g. of fat in milk is determined by use of a number of specific filters from the absorbance in the milk sample measured relative to a reference, such as a reference sample, e.g. a sample of pure water. This is a well-known technique, e.g. as described in U.S. Pat. No. 4,236,075, which has been applied for analysis of food products for more than 20 years.

The analysis of milk is now increasingly being carried out by use of FTIR instruments covering a broad frequency range of the IR spectrum, c.f. international patent application No. PCT/DK96/00068 published as WO 96/24832. The measured spectra of a plurality of known samples are used to let the instrument "learn" how to interpret newly measured spectra of unknown samples. Such learning can be accomplished by multivariate calibration in several ways, e.g. by Principal Component Regression (PCR), Partial Least Squares regression (PLS), Multiple Linear Regression (MLR), Artificial Neural Network (ANN), etc. A great advantage when using FTIR instruments is that such instruments may be standardised so that the same calibration can be applied to a plurality of standardised instruments.

FTIR instruments are costly. Accordingly, there is still a need for the less expensive filter instruments applying a few or at least a limited number of optical filters. It has so far been impossible to standardise such instruments, implying that every instrument must be calibrated separately, and when a measurement cell or any other change in the optical system has been carried out during maintenance, the instrument requires new calibrations.

In this context a calibration means the derivation of a mathematical expression, such as a functional relationship, enabling a prediction of a concentration of a specified constituent from a number of determined absorbance values.

The absorbance, a, is defined as the absorption relative to a reference. The absorbance is determined from signals $I_s$, $I_o$, measured by a detector, (e.g. as a measure in mV or mA), when measuring an unknown sample and a reference, respectively.

$$a = \log_{10}(I_o/I_s)$$

When the absorbance values, a, have been determined for at least one, preferably a plurality of filters, e.g. four filters, the concentration c of a specific component may be predicted from an expression such as:

$$c = b_1 * a_1 + b_2 * a_2 + b_3 * a_3 + b_4 * a_4$$

The b-coefficients in the above equation may be determined by multivariate calibration after measuring a number of samples having various known concentrations of specific constituents. Calibrations are made for specific constituents, e.g. the fat content in milk.

The task of providing a good calibration for an instrument can be very laborious as it usually requires a great number of calibration samples having known concentration of a constituent in question. The calibration samples typically have to be analysed by tedious conventional methods and accordingly, a calibration sample is typically expensive. Since the calibration sample is typically a food product, e.g. a diary product, the durability is rather limited and new test samples have to be provided for each calibration.

Often, a calibrated instrument has to be re-calibrated from time to time. As an example, parts of the instrument, e.g. the cuvette or a detector may be replaced during repair or service. The new part may have a characteristic different from the characteristic of the previous part and accordingly, the relationship between the detected signal and the concentration of the constituent is different.

DESCRIPTION OF THE INVENTION

It is an object of the invention to provide a method whereby a recalibration is avoided. The method should be easy to carry out by use of substances which are easy to handle and easy to store over time.

Accordingly, the present invention relates to a method of determining a constituent of a sample. The method comprises correcting a relative response value, e.g. a response value for milk relative to a response value for water. The method is applicable in an instrument of the kind measuring a constituent of a sample by exposing the sample to electromagnetic radiation, in particular infrared radiation. By means of the instrument, a response value from the radiation of a sample of the object or fluid in question is obtained and a relative response value is calculated by comparing the obtained response value with a response value from a reference sample, e.g. water. The method comprises the steps of:

when the instrument is in a first state in which it is newly calibrated:
   obtaining a first response value for a first adjustment sample, and
   obtaining a second response value for a first reference sample,
when the instrument is in a state different from the first state:
   obtaining a third response value for a adjustment sample having the same composition as the first adjustment sample, obtaining a fourth response value for a reference sample having the same composition as the first reference sample, from the response values, determining a gain representing the relationship between a first relative response value being the ratio between the first and the second response values and a second relative response value being the ratio between the third and fourth response values, respectively, and for a sample, correcting the relative response value by means of the gain in order to determining a constituent of the sample in question, wherein the first reference sample comprises a first substance having a first absorbing characteristic and the first adjustment sample comprises the first substance and a second substance having a second absorbing characteristic.

The first and second absorbing characteristic should be mutually different.

Since the adjustment sample comprises a second substance having a second absorbing characteristic different from the first substance, it is achieved that a response of the adjustment sample is different from a response of the reference sample. Accordingly a response of the adjustment sample relative to a response of the reference sample gives a relative response representing an absolute value, which value can be used to determine a gain. The gain is a value, which is indicative of the relative response value for a specific sample, which value would have been obtained at the time when the apparatus was calibrated, relative to the presently obtained relative response value of the same sample. Accordingly, the relative response values achieved for a sample may be changed into the corresponding relative response value the same sample would have given at the time when the apparatus was calibrated and that relative response value may be used for determining a constituent of the sample using the original calibrations.

The method may further comprise the step of calibrating the instrument. The calibration must be performed when the instrument is in the first state, i.e. at the time when the first and second response values are obtained. In that way it is ensured that the calibration model is coherent with the response values of the reference sample and the adjustment sample. The calibration could comprise the steps of:

obtaining a fifth response value for a sample having well known properties, e.g. milk which have been analysed in a traditional and tedious way, and from the first response, the fifth response and the known properties, determining a calibration function being a functional relationship between properties of a sample and the a relative response value being a response value for the sample, relative to a response value for the reference sample.

Further the invention relates to a method of correcting an absorbance value for a spectrometer, said method comprising the steps of:

when the instrument is in a first state:
calibrating the spectrometer, and
obtaining a first absorbance value for a first adjustment sample, said absorbance value being the absorbance relative to a first reference sample,
or vice versa (calibrating afterwards), when the instrument is in a state different from the first state:
obtaining a second absorbance value for a second adjustment sample having the same composition as the first adjustment sample, said second absorbance value being the absorbance relative to a second reference sample, having the same composition as the first reference sample from the absorbance values, determining a gain representing the ratio between the first and second absorbance value, and for future samples to be analysed, correcting the obtained absorbance value by means of the gain, wherein the absorbance value of the adjustment sample is considerable different from zero in the spectral range covered by the spectrometer.

Preferably, the first reference sample comprises a first substance having a first absorbing characteristic and the first adjustment sample comprises the first substance and a second substance having a second absorbing characteristic in the spectral range covered by the spectrometer. The absorbing characteristics of the first and second substances should be mutually different.

Since the adjustment sample comprises a second substance having a second absorbing characteristic different from the first substance, it is achieved that an absorbance of the adjustment sample is a value different from zero, which value can be used to determine a gain. The gain is a value, which is the ratio between the absorbance of a specific sample that would have been obtained at the time when the spectrometer was calibrated, and the presently obtained absorbance of the sample. Accordingly, the new absorbance value achieved for a sample may be changed into the corresponding (i.e. corrected) absorbance value the same sample would have given at the time when the spectrometer was calibrated, and this corrected absorbance may be used for determining a concentration of a constituent of the sample, using the original calibration.

Accordingly, the present invention is an alternative to a re-calibration, the instrument may be "standardised" or adjusted, i.e. the data processing of the detected signals is adjusted to provide data that are compliant with the calibration. The advantage being, that a re-calibration is avoided. The calibration of an instrument may be used over time even though the response of the detector changes due to wear or repair.

Accordingly, the adjustment of the measured absorbance values requires an easily reproducible adjustment sample or an adjustment sample that may be stored over time without changing its absorbing properties and which has a significant different absorbing characteristic compared with the absorbing characteristic of the reference sample.

The method is particularly advantageous for fluid samples.

The method may further comprise the step of calibrating the instrument. The calibration may be performed when the instrument is in the first state, i.e. at the time when the first absorbance is obtained. In that way it is ensured that the calibration model is coherent with the absorbance of the adjustment sample. The calibration could comprise the steps of:

obtaining a third absorbance value for a calibration sample having well known properties, e.g. milk which have been analysed in a traditional and tedious way, and from the third absorbance value and the known properties, determining a calibration function being a functional relationship between properties of a sample and an absorbance value.

Preferably, the first substance is pure water and the second substance is a salt such as NaCl, KaCl, MgCl, a salt of Chloride, Bromide etc. Preferably, the adjustment sample comprises pure water mixed with 12% NaCl.

Preferably the first substance has a more absorbing characteristic than the second substance in the spectral range covered by the spectrometer. As an example, the first substance may be pure water and the second substance may be a saline solution. The first substance may similarly be a silicone oil or a similar substantially transparent liquid. However, pure water being a relatively highly absorbing substance is therefor considered to be the preferred substance for carrying out the invention.

In particular, it is preferred to provide a first substance, which absorbs radiation differently from the second substance over the entire IR-frequency range. In that case, the relative absorption between the two substances may be determined over the entire IR-frequency range, allowing the instrument to be adjusted for any frequency within the IR-frequency range.

According to a preferred embodiment of the invention, the second substance is selected from a compound, which absorbs substantially no radiation within the IR-frequency range. As an example, NaCl dissolved in water will, up to a certain concentration, aprox. 18% weight percentage, be completely ionised and since the Na-ions and Cl-ions absorbs substantially no IR-radiation, the saline solution will absorb IR-radiation with the same absorption pattern over the IR-spectrum but the solution will be almost equally less absorbing for all frequencies within the IR-spectrum. In fact the saline solution—in respect of its absorbing properties—is similar to pure water with a reduced "density", i.e. some of the water molecules have been displaced by the ions. Accordingly, a specifically preferred embodiment of the invention relates to the use of a reference sample being water with a first NaCl concentration and the adjustment sample being water with a second concentration. The second concentration being higher than the first concentration—in fact, the first concentration is preferably substantially zero.

In order to allow storage of the substances over time, the first and/or second substance may preferably be provided to the user, e.g. in a small ampoule or sachet. Preferably an additive for preserving the absorbing characteristics of the substance is added.

According to an alternative embodiment, the NaCl solution in water may be replaced with any salt solution comprising Chloride or Bromide, e.g.: NaCl, KaCl and MgCl.

The second substance of the adjustment sample preferably constitutes in the range of 1-24 weight percentage, such as in the range of 6-18 weight percentage, such as in the range of 10-14 weight percentage such as in the size of 12 weight percentage of the second substance in relation to the first substance.

According to an alternative embodiment, the first substance comprises water and the second substance comprises alcohol.

According to yet an alternative embodiment, the first substance comprises water and the second substance comprises silicone oil.

According to another aspect, the present invention relates to a spectrometer arranged to determine the absorbance of a sample, and for determining a concentration of a constituent of a sample said spectrometer comprising:

at least one electromagnetic source adapted to expose the sample to a specific spectral range of electromagnetic radiation, in particular infrared light, at least one filter means able to select a specified spectral range, at least one sample compartment for containing a sample, at least one detector for recording and converting optical signals into electrical signals, means for digitising the signals, processing means adapted to process the digitised signals in order to determine an absorbance of a measured sample, storage means adapted for storing calibration coefficients for a function defining the relationship between an absorbance from a sample and a concentration of a constituent of the sample, the storage means being further adapted for storing a first absorbance from a first adjustment sample, and a second absorbance from a second adjustment sample, and processing means adapted to calculate the ratio ($A_{nadj}/A_{mew\ adj}$) between the first and the second absorbance of an adjustment sample in order to determine a gain factor ($g_n$) to be stored in the storage means, the processing means further being adapted to modify the absorbance values measured for future samples by the gain factor ($g_n$).

Preferably, the components of the spectrometer are adapted to the infrared range, comprising NIR and/or MID-IR). Preferably, the spectrometer comprises a plurality of filters and detectors each being adapted primarily to obtain a signal within a specified frequency range for the specific combination of a filter and a detector. The frequency range could be selected within a frequency range wherein a specific constituent in question is particularly absorbing. A presently preferred waveband is the mid-infrared waveband from about 2 μm to 15 μm, and preferably limited to the waveband range from 2,5 μm to 10 μm, and preferably comprising a few selected band pass-filters for narrow wavebands within said range. Examples of preferred average values for waveband ranges (in cm−1) are: 1045 (lactose) 1523 (protein) 1496 (neutral reference region) 1727 (fat A) and 2853 (fat B).

The spectrometer may have an internal processor for processing the signals in order to determine the concentration of the constituents in questions and/or the spectrometer may be provided with an interface for transfer of data between the spectrometer and an external computer system. The external computer system may as an example be used for storage of date, e.g. for the purpose of documentation, quality control etc.

Preferably, the spectrometer is further provided with printing means and/or with a screen adapted to printout the concentration of the constituent of the fluid sample, e.g. for the documentation of the quality of the product in question.

According to a preferred embodiment, the spectrometer further comprises storage means is further adapted for storing the result of the analysis, i.e. the concentration of the constituent of the fluid sample. The storage means may e.g. be a regular hard drive for a computer system, e.g. comprising a database management system.

The spectrometer is provided with a measurement chamber or a so called cuvette for containing the fluid sample said measurement chamber being provided with at least one window enabling a beam of electromagnetic radiation to enter and leave the sample. The measurement chamber may comprise two substantially planar glass plates, typically $CaF_2$, which is transparent to IR light, arranged in parallel with a mutual distance in the range of 10-100 μm, such as in the range of 20-80 μm, such as in the range of 30-60 μm, such as in the range of 35-55 μm, such as 50 μm.

The spectrometer may further be provided with storage means for storing the fluid sample to be analysed. The storing means could be a regular bottle connected to an inlet for pumping the sample from the bottle and into the cuvette. Alternatively, the spectrometer may have a connection to a process flow line, e.g. to a flow line of a dairy plant and be provided with means for automatically taking out samples from the flow line.

Dairy products like milk, have relatively large and unevenly distributed fat particles from the natures side. It is therefore an advantage to provide homogenisation means between the storage means or flow line connection and the cuvette. The homogenisation means may be constituted by an object with a small hole. when the sample, e.g. milk, is pressed through the hole under high pressure, the fat particles will be destroyed and the fat will be distributed more evenly in the milk.

The spectrometer may further be provided with storage means for storing the fluid reference sample and the fluid adjustment sample. The storage means may be connected directly with the measurement chamber to allow the fluids to be pumped directly from the storage means and into the chamber.

The spectrometer may preferably be provided with a pumping system capable of providing a fluid from one of the storage means and to the chamber and preferably with a pumping system capable of maintaining a relatively constant fluid pressure in the chamber.

The spectrometer may further be provided with storage means for storing waste fluid from samples that have been analysed. The fluid may be pumped from the measurement chamber to the storage means for storing waste fluid samples either by the pressure of the next sample being pumped into the chamber or by a separate pump arranged for emptying the content of the chamber into the waste fluid storage means.

The spectrometer may further be provided with automatic cleaning means for cleaning the measurement chamber, hoses and homogenising means. The cleaning means may comprise a separate pumping system and/or a separate storage tank for storage of a cleaning fluid.

According to a preferred embodiment of the invention, the spectrometer is provided with a watch. The watch may e.g. be used for recording in the memory of a computer system or on a printed label, a record of the fluctuations of the concentration of the constituent over time. This may in particular be an advantage in connection with line flow control, wherein the spectrometer is directly connected with means for taking fluid samples from a flow line, e.g. of a diary plant.

DETAILED DESCRIPTION OF THE INVENTION

Figure 2:
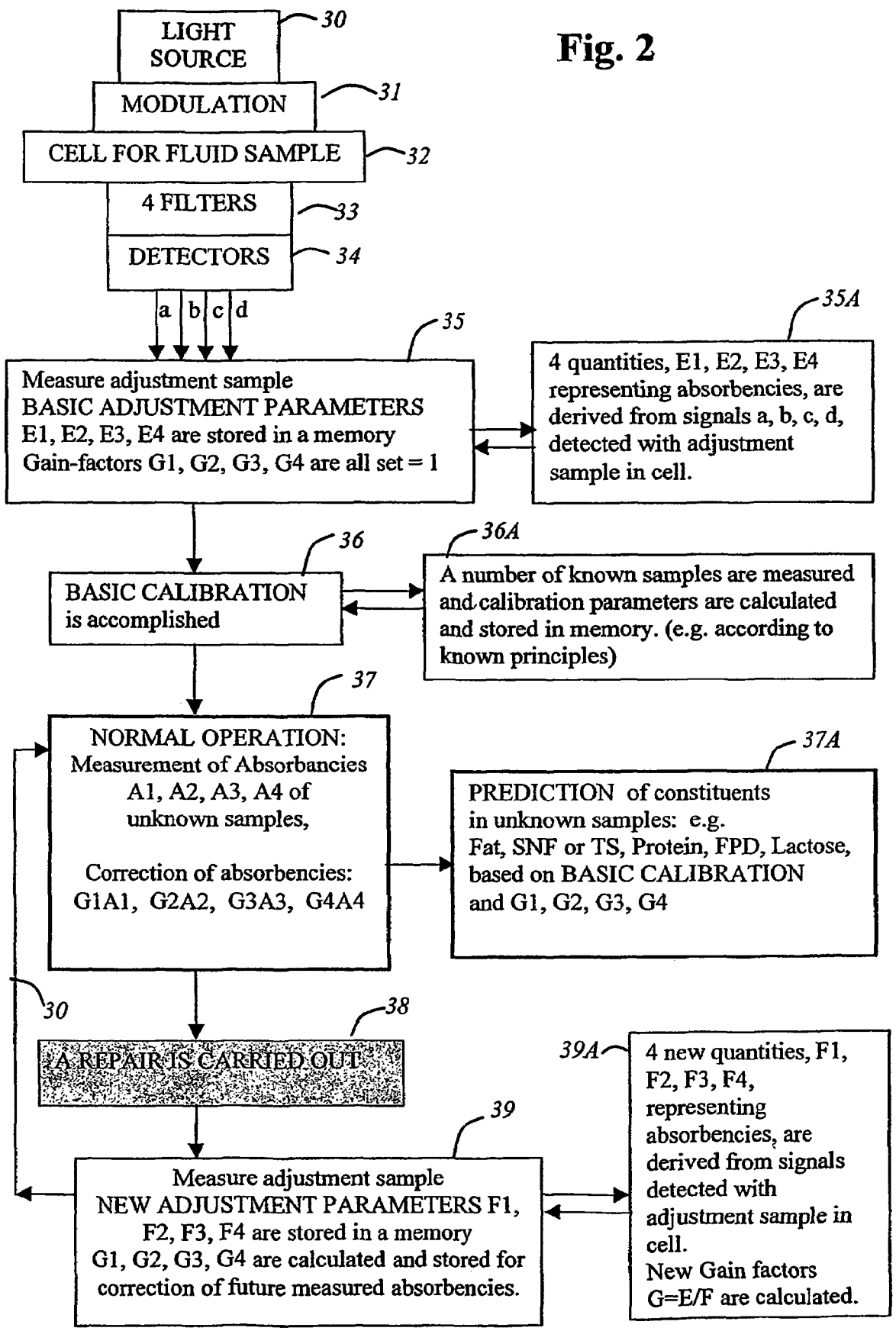

A preferred embodiment of the invention will now be described in details relative to an IR-instrument for analysing milk products and with reference to the drawing in which FIG. 1 shows a schematic diagram of an instrument according to the invention, and FIG. 2 shows a flow diagram of the method according to the invention.

FIG. 1 shows an example of a preferred spectrometer for performing a quantitative determination of a constituent according to the invention. The spectrometer comprises a pipette 10 for aspirating a sample from a container 11, tubes or hoses 12 carrying the sample through an intake valve 13 to a heat exchanger unit 14. The sample may preferably be pumped by means of a peristaltic pump 15. After the heat exchanger unit 14, the sample is pumped through an inline filter 16 and through a homogenising unit 17. The homogenising unit 17 is provided with a stone hole 18 in the end part 19, though which stone hole the fluid sample is pumped in order to homogenise the sample. From the homogenising unit, the sample is pumped to a measurement cuvette 20. The measurement cuvette 20 comprises two parallel glass plates 21, 22, typically $CaF_2$, which is transparent to IR light, defining a light path therein between. The light path may be in the size of approximately 50 μm. The spectrometer further includes an IR source 23 and optical equipment for the transmission of infrared light. IR detection means 24 is adapted to detect the light passing through the cuvette 20. The spectrometer is preferably provided with at least four detection means corresponding to detection of the light within four well-defined wavebands (in FIG. 1, only one detection means is shown). Filters (not shown) may be arranged in front of each of the four detection means in order to filter out at least a major part of the light having a wavelength outside the scope of the particular detecting means. Alternatively, four or more filters may be movably arranged so as to allow each filter to be inserted in front of the detection means individually. The spectrometer further comprises data recording means and calculator means (not shown) connected to the detection means. As an example, the detection means may be connected to a regular computer system with software adapted to process the response from the detection means and from that response to calculate the constituent(s) in question.

The computer system (not shown) preferably comprises display means and input means, e.g. as given by a regular PC with an Intel Pentium processor.

After the detection of the radiation, the fluid is washed out of the measurement cuvette by means of a rinse liquid taken from a corresponding rinse container 25. The waste fluid is discharged into a waste container 27 for its disposal.

The back-pressure regulator 26 provides sufficient back-pressure to maintain an amount of the sample liquid in the cuvette under well-defined pressure during measurement.

FIG. 2 shows a flow diagram illustrating the method. As indicated in the step 30, an IR light source generates light in front of a rotating "fan" modulating (step 31) the light beam by a specified frequency, e.g. 10 hertz, a modulation that is necessary for the detection circuitry. The modulated light passes through the cuvette (step 32). In the presently preferred embodiment, the light passes through a set 4 filters (step 33) in parallel arranged behind the cuvette, right in front of four detectors (step 34), each detector corresponding to one filter, i.e. corresponding to light primarily within one specified waveband.

The absorbance values for an adjustment sample are measured by detecting the light intensities, e.g. in millivolts (mV), and processing the signals, a, b, c and d, in the processing means in order to determine the absorbance values E1-E4 in each of the wavebands of the four filters. The values E1-E4 are stored in the memory of the spectrometer (step 35, 35A).

Subsequently, or just before, absorbance values are measured with different known samples, i.e. calibration samples wherein the amounts of a specific constituent are known. Based on the known amount of a specific constituent and the measured absorbance, the spectrometer is calibrated (step 36-36A). After the calibration, the spectrometer is capable of determining the concentration of a constituent of an arbitrary sample based on the measurement of the absorbance for light passing through the sample (step 37-37A).

Over time, certain characteristics of the spectrometer may change. As an example, the emitted light intensity of the lamp may change and possibly, the intensity does not change equally over the entire frequency range of the lamp. The sensitivity of the detector or detectors may change and the cuvette glass may become dim so that the glass itself absorbs or reflects more and more of the radiation. However, since the concentration of a constituent of the sample is always determined from the absorbance, i.e. the absorption relative to a reference sample, e.g. water, the error is typically negligible. If the spectrometer is being repaired, in particular if the cuvette is replaced, the characteristics of the spectrometer may change more importantly. The cuvette defines a spacing between two glass plates. Typically, the spacing is in the range of 30-60 μm. In practise, it is impossible to provide two cuvettes defining the same spacing between the glass plates. Usually, the distance may vary up to 10 μm. Evidently, the absorption of the light passing through the fluid sample depends on the spacing between the glass plates, i.e. the absorption in the sample is proportional to the distance the light must pass through the sample. Accordingly, the spectrometer must be readjusted after repair (step 38, 39-39A). The new adjustment is carried out by measuring 4 new quantities F1, F2, F3, F4, representing absorbance in each waveband of the four filters. The measured values are stored in the memory and new gain factors G=E/F are calculated and stored. Then the instrument is again ready for normal operation (step 37-37A) using the basic calibration.

In the following exemplification, the determination and use of one gain factor is explained.

1. The instrument is calibrated, i.e. the relationship between the concentration c, of a constituent in a sample and the corresponding absorbance A is determined: The result is a function $F(A_1)$=the concentration, e.g. the fat content, wherein $A_1$ denotes the absorbance determined with the one-and-only or first filter/detector combination). Per definition the absorbance $A=\log_{10}(I_0/I_s)$ wherein $I_0/I_s$ is derived from the signals measured by the detector, e.g. as a measure in mV, when measuring an sample and a reference, respectively.

2. The absorbance of an adjustment sample is determined. As an example, a 12% NaCl in water solution is measured in the spectrometer. The absorbance E is stored in a memory.

3. The spectrometer is used for quantitative determination of the content of constituents in samples. The measured absorbance A are adjusted into A'=g*A, wherein the gain factor originally has the value 1 (g=1). That means the content is determined from the measured absorbance without any correction and from the original calibration.

4. After a period of time, may be a year, maintenance is carried out. The cuvette is replaced by a new cuvette.

5. The absorbance of a similar adjustment sample, i.e. a new absorbance of 12% NaCl in water solution, is determined. The absorbance F is stored, at least temporarily, in a memory.

6. A new gain factor is calculated as E/F. The new gain factor is stored in a memory.

7. The spectrometer may again be used for quantitative determination of the content of constituents in samples. The measured absorbance A are adjusted into A'=g*A wherein g=E/F. That is the content is determined from the measured absorbance with correction by gain factor g and from the original calibration.

8. After a period of time, may be another year, a second maintenance is carried out. The cuvette is replaced by a new cuvette.

9. The absorbance of a similar adjustment sample, i.e. a new absorbance of 12% NaCl in water solution, is determined. The absorbance F is stored, at least temporarily, in a memory.

10. A new gain factor is calculated as E/F. The new gain factor is stored in a memory.

11. . . . and so on. The same calibration may be used forever.

The same procedure applies for the presently preferred embodiment, having four filters. The only difference is that each measurement of a sample provides four values for an absorbance in each of the four wavebands defined by the four filters. The four values E1, E2, E3, E4 of absorbance of a first adjustment sample (e.g. 12% NaCl in water solution), are determined, each value corresponding to one of the filters. The values are stored in the memory of the device for later use. Gain factors $g_1$-$g_4$ all equals 1 for a newly calibrated instrument.

After a repair four new values F1, F2, F3, F4 of absorbance of an adjustment sample (similar to the first adjustment sample) are determined. New gain factors g1, g2, g3, g4, are calculated and stored.

Based on the calibration function F, gain factors $g_n$ and absorbance values measured for arbitrary samples, the spectrometer may be used for quantitative determination of the content of constituents in samples.

In the case of a spectrometer having n combinations of filters and detectors, the calibration may be defined be a function $F(g_1 A_1, ,, g_n A_n)$ determining the content of a constituent, wherein $A_n$ denotes the absorbance determined with the n'th filter/detector combination). $g_1$-$g_n$ all equals 1 for a newly calibrated instrument. Right before or after calibration an adjustment sample is measured.

The only difference from the example with one filter is that each measurement of a sample provides n absorbance values for the n wavebands defined by the n filters. The n absorbance values (E1, E2, . . . , En) of a first adjustment sample (e.g. a 12% NaCl in water solution), are determined, each value corresponding to one of the filters. The values are stored in the memory of the device for later use.

After a repair n new values (F1, F2, . . . , . . . Fn) of absorbance of an adjustment sample (similar to the first adjustment sample) are determined. New gain factors g1, g2, . . . , . . . gn, are calculated and stored.

$$g = \text{gain factor} = E/F = A_{adj}/A_{new\ adj}$$

According to the present invention the determined absorbance values $A_1$-$A_n$ are multiplied by gain factors $g_1$-$g_n$. $g_1$-$g_n$ denotes the first to n'th gain factor.

For each measurement of arbitrary samples thereafter, the original calibration is applied with the latest calculated g values (gain values), i.e. the function $F(g_1 A_1, ,, g_n A_n)$.

The invention claimed is:

1. A method of correcting a relative response value for an instrument of the kind capable of determining a constituent of a sample from a predetermined functional relationship between constituents of the sample and a relative response value being a response value from the exposure of the sample to electromagnetic radiation relative to the response value from the exposure of a reference sample to electromagnetic radiation, said method comprising the steps of:
when the instrument is in a first state in which it is newly calibrated:
obtaining a first response value for a first adjustment sample, and obtaining a second response value for a first reference sample, when the instrument is in a state different from the first state:

obtaining a third response value for a adjustment sample having the same composition as the first adjustment sample, obtaining a fourth response value for a reference sample having the same composition as the first reference sample, from the response values, determining a gain representing the relationship between a first relative response value being the ratio between the first and the second response values and a second relative response value being the ratio between the third and fourth response values, respectively, and for a sample, correcting the relative response value by means of the gain in order to determine a constituent of the sample in question, wherein the first reference sample comprises a first substance having a first absorbing characteristic and the first adjustment sample comprises the first substance and a second substance having a second absorbing characteristic.

2. A method according to claim 1, further comprising the steps of, when the instrument is in the first state:

obtaining a fifth response value for a sample having well known properties, and from the second response, the fifth response and the known properties, determining a calibration function being a functional relationship between properties of a sample and a relative response value being a response value for the sample, relative to a response value for the reference sample.

3. A method according to claim 1, wherein the samples are fluid samples.

4. A method according to claim 1, wherein the first substance has a more absorbing characteristic than the second substance in the spectral range covered by the spectrometer.

5. A method according to claim 1, wherein the first substance absorbs radiation differently from the second substance over the entire IR-frequency range.

6. A method according to claim 1, wherein the second substance absorbs substantially no radiation within the IR-frequency range.

7. A method according to claim 1, wherein the first substance comprises water.

8. A method according to claim 7, wherein the first substance further comprises an additive for preserving the absorbing characteristics of the water.

9. A method according to claim 1, wherein the second substance of the adjustment fluid is a salt dissolved in the first substance.

10. A method according to claim 9, wherein the salt comprises Chloride or Bromide.

11. A method according to claim 9, wherein the salt is selected from a group consisting of: NaCl, KaCl and MgCl.

12. A method according to claim 9, wherein the second substance of the adjustment sample constitutes in the range of 1-24 weight percentage, such as in the range of 6-18 weight percentage, such as in the range of 10-14 weight percentage such as in the size of 12 weight percentage of the of the second substance in relation to the first substance.

13. A method according to claim 1, wherein the first substance comprises water and the second substance comprises alcohol.

14. A method according to claim 1, wherein the first substance comprises water and the second substance comprises silicone oil.

15. A method of correcting an absorbance value for a spectrometer, said method comprising the steps of:

when the instrument is in a first state:

calibrating the spectrometer, and obtaining a first absorbance value for a first adjustment sample, said absorbance value being the absorbance relative to a first reference sample, or vice versa (calibrating afterwards), when the instrument is in a state different from the first state:

obtaining a second absorbance value for a second adjustment sample having the same composition as the first adjustment sample, said second absorbance value being the absorbance relative to a second reference sample, having the same composition as the first reference sample from the absorbance values, determining a gain representing the ratio between the first and second absorbance value, and for future samples to be analysed, correcting the obtained absorbance value by means of the gain, wherein the absorbance value of the adjustment sample is considerably different from zero in the spectral range covered by the spectrometer.

16. A method according to claim 15, wherein the first reference sample comprises a first substance having a first absorbing characteristic and the first adjustment sample comprises the first substance and a second substance having a second absorbing characteristic in the spectral range covered by the spectrometer.

17. A method according to claim 15, further comprising the steps of, when the instrument is in the first state:

obtaining a third absorbance value for a calibration sample having well known properties, and from the third absorbance value and the known properties, determining a calibration function being a functional relationship between properties of a sample and an absorbance value.

18. A spectrometer arranged to determine the absorbance of a sample, and for determining a concentration of a constituent of a sample said spectrometer comprising:

at least one electromagnetic source adapted to expose the sample to a specific spectral range of electromagnetic radiation, in particular infrared light, at least one filter means able to select a specified spectral range, at least one sample compartment for containing a sample, at least one detector for recording and converting optical signals into electrical signals, means for digitising the signals, processing means adapted to process the digitised signals in order to determine an absorbance of a measured sample, storage means adapted for storing calibration coefficients for a function defining the relationship between an absorbance from a sample and a concentration of a constituent of the sample, the storage means being further adapted for storing a first absorbance from a first adjustment sample, and a second absorbance from a second adjustment sample, and processing means adapted to calculate the ratio ($A_{nadj}/A_{mew\ adj}$) between the first and the second absorbance of an adjustment sample in order to determine a gain factor ($g_n$) to be stored in the storage means, the processing means further being adapted to modify the absorbance values measured for future samples by the gain factor ($g_n$).

19. A spectrometer according to claim 18, comprising a plurality of filters and detectors each of which being adapted primarily to obtain a signal within a specified frequency range for the specific combination of a filter and a detector.

20. A spectrometer according to claim 19, wherein the components of the spectrometer are adapted to the infrared range, comprising NIR and/or MID-IR).

21. A spectrometer according to claim 18, comprising an interface for transfer of data between the spectrometer and an external computer system.

22. A spectrometer according to claim 18, comprising an interface for an operator, the interface comprising printing means adapted to printout the concentration of a constituent of the fluid sample.

23. A spectrometer according to claim 22, wherein the interface further comprises a screen for displaying the concentration of a constituent of the fluid sample.

24. A spectrometer according to claim 18, wherein the storage means is further adapted for storing the concentration of a constituent of the fluid sample.

25. A spectrometer according to claim 18, comprising a measurement chamber for containing the fluid sample said measurement chamber being provided with at least one window enabling a beam of electromagnetic radiation to enter and leave the sample.

26. A spectrometer according to claim 25, further comprising cleaning means for cleaning the measurement chamber.

27. A spectrometer according to claim 18, comprising storage means for storing the fluid sample.

28. A spectrometer according to claim 18, comprising storage means for storing the fluid reference sample.

29. A spectrometer according to claim 18, comprising storage means for storing the fluid adjustment sample.

30. A spectrometer according to claim 18, comprising fluid pumping means for pumping a fluid sample from the storing means to the measurement chamber.

31. A spectrometer according to claim 18, comprising storage means for storing waste fluid samples.

32. A spectrometer according to claim 31, comprising fluid pumping means for pumping a fluid sample from the measurement chamber to the storage means for storing waste fluid samples.

33. A spectrometer according to claim 18, further comprising a homogenising unit for homogenising the fluid sample prior to the determining of the concentration of a constituent of the fluid sample.

34. A spectrometer according to claim 18, further comprising a watch and wherein the processing means is adapted to record fluctuations of the concentration of a constituent over time.

* * * * *